United States Patent
Andrews et al.

(10) Patent No.: US 9,709,512 B2
(45) Date of Patent: Jul. 18, 2017

(54) MULTILEVEL COMPUTED TOMOGRAPHY FOR RADIALLY-SHIFTED FOCAL SPOTS

(71) Applicants: VARIAN MEDICAL SYSTEMS, INC., Palo Alto, CA (US); University Of Utah Research Foundation, Salt Lake City, UT (US)

(72) Inventors: Gregory C. Andrews, Draper, UT (US); Dominic J. Heuscher, Park City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 282 days.

(21) Appl. No.: 14/013,995

(22) Filed: Aug. 29, 2013

(65) Prior Publication Data
US 2015/0063532 A1  Mar. 5, 2015

(51) Int. Cl.
*G06T 11/00* (2006.01)
*G01N 23/04* (2006.01)

(52) U.S. Cl.
CPC .......... *G01N 23/046* (2013.01); *G06T 11/006* (2013.01); *G01N 2223/04* (2013.01); *G06T 2211/421* (2013.01)

(58) Field of Classification Search
CPC .... G01T 11/003; G01T 11/006; G01T 11/008; G01N 23/046; G01N 2223/076; G01N 2223/419; G01N 23/223; A61B 6/4021; A61B 6/032; A61B 6/5205; A61B 6/03; A61B 6/025; A61B 5/0073; G06T 11/006; G06T 11/003; G06T 11/005;
(Continued)

(56) References Cited

U.S. PATENT DOCUMENTS 5,590,164 A * 12/1996 Kawai et al. ..................... 378/4
6,008,813 A * 12/1999 Lauer et al. .................. 345/424
(Continued)

OTHER PUBLICATIONS

Flohr, T. G., Stierstorfer, K., Ulzheimer, S., Bruder, H., Primak, A. N., Mccollough, C. H., "Image reconstruction and image quality evaluation for a 64-slice CT scanner with z-flying focal spot", Medical Physics, 32, 2536-2547 (2005).
(Continued)

*Primary Examiner* — Dani Fox
(74) *Attorney, Agent, or Firm* — Thorpe North & Western, LLP

(57) ABSTRACT

In one example embodiment, a method of volumetric image reconstruction of an examination region includes directing x-rays from an anode of an x-ray device towards the examination region from multiple positions relative to the examination region, including multiple focal spot positions radially shifted relative to the anode. X-rays that have passed through the examination region are detected and first multiple x-ray attenuation values are determined for each of the multiple positions. The first multiple x-ray values are based at least in part on the detected x-rays. Second multiple x-ray attenuation values associated with multiple levels are determined. The second multiple attenuation values are based at least in part on the first multiple attenuation values and the multiple positions. The method further includes generating a volumetric image reconstruction of the examination region based at least in part on the second multiple x-ray attenuation values.

19 Claims, 10 Drawing Sheets

(58) Field of Classification Search
CPC ......... G06T 11/008; G06T 2207/10081; G06T 2207/100072; G06T 2211/40
See application file for complete search history.

(56) References Cited

U.S. PATENT DOCUMENTS

| | | | | |
|---|---|---|---|---|
| 6,292,538 | B1* | 9/2001 | Hell | H01J 35/14 378/137 |
| 7,769,129 | B2* | 8/2010 | Hein et al. | 378/19 |
| 7,809,100 | B2* | 10/2010 | Shechter | 378/4 |
| 7,949,090 | B2* | 5/2011 | Hagiwara et al. | 378/15 |
| 2002/0186816 | A1* | 12/2002 | Freudenberger | H01J 35/305 378/144 |
| 2004/0190682 | A1* | 9/2004 | Deuringer | H05G 1/52 378/137 |
| 2004/0208287 | A1* | 10/2004 | Deuringer | H05G 1/52 378/121 |
| 2010/0067651 | A1* | 3/2010 | Hsieh | A61B 6/032 378/17 |
| 2011/0135066 | A1* | 6/2011 | Behling | H01J 35/10 378/138 |
| 2012/0027164 | A1* | 2/2012 | Caiafa | H01J 35/10 378/16 |
| 2012/0128122 | A1* | 5/2012 | Kautz | A61B 6/4021 378/16 |
| 2012/0163530 | A1* | 6/2012 | Sainath | A61B 6/027 378/5 |
| 2012/0275562 | A1* | 11/2012 | Kautz | A61B 6/032 378/20 |

OTHER PUBLICATIONS

Ulzheimer, Stefan, Ph.D., "Interleaved Volume Reconstruction (IVR), 2012, http://www.medical.siemens.com/siemens/en_US/gg_ct_FBAs/files/Perspective/A911IM-CT-121797-P1-4A00_Whitepaper_IVR_DD_V6.pdf".

Ulzheimer, Stefan and Flohr, Thomas, "Multislice CT: Current Technology and Future Developments, Multislice CT", 3rd ed. 2009, pp. 3-23, pub.: Springer Berlin Heidelberg.

Utrup, Steven j. and Philips, Kevin M. brown, "Quantification and Elimination of Windmill Artifacts in Multi Slice CT", Proc. of SPIE vol. 6913, Healthcare Medical Imaging 2008: Physics of Medical Imaging 691338.

* cited by examiner

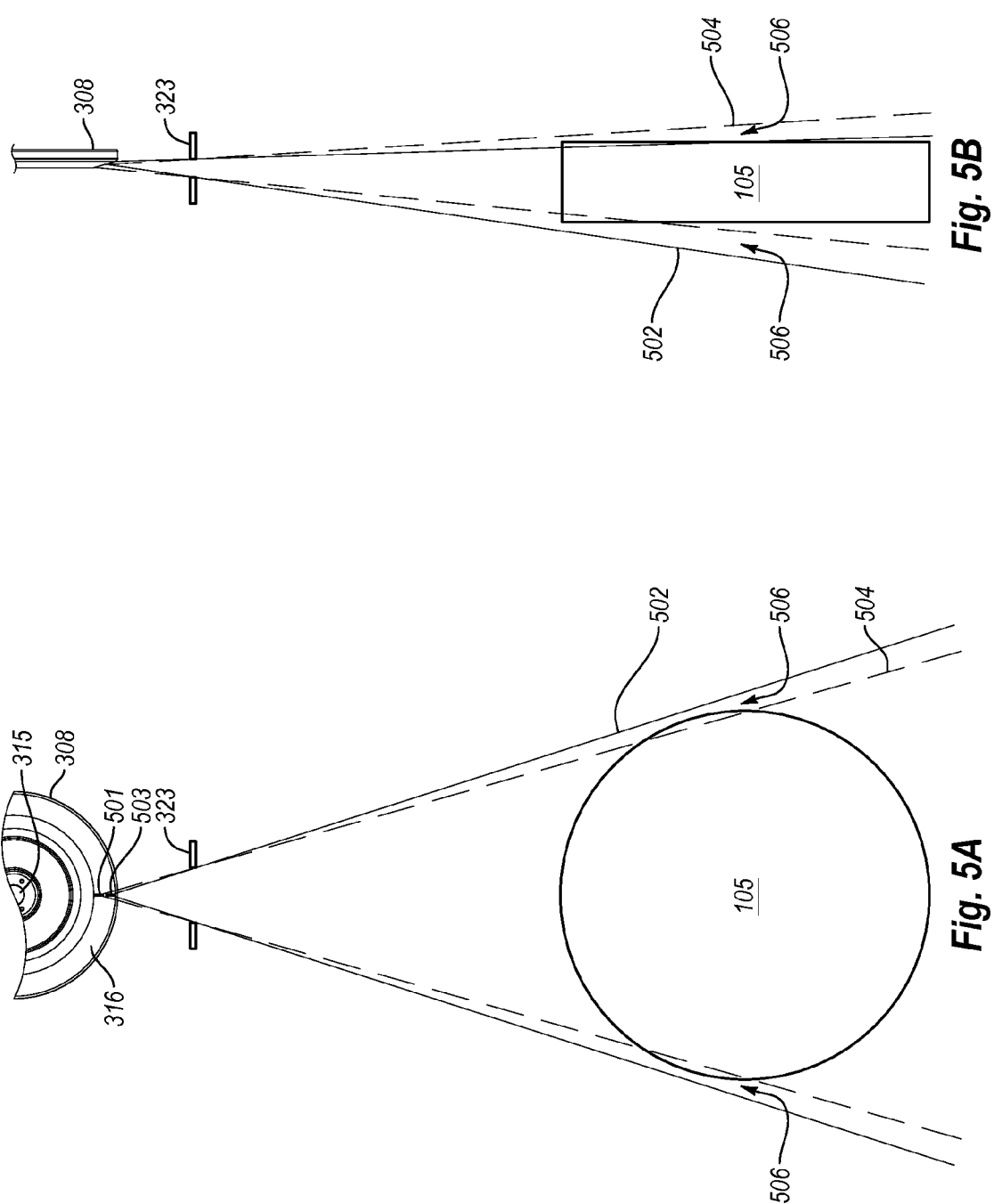

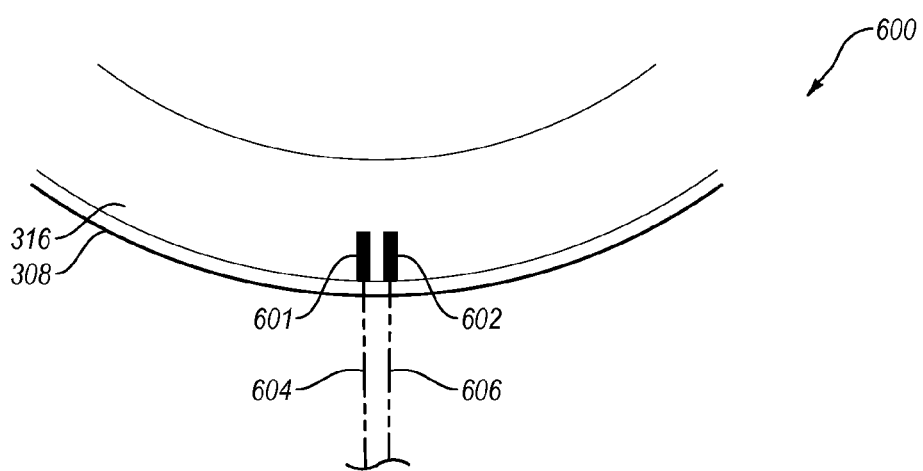
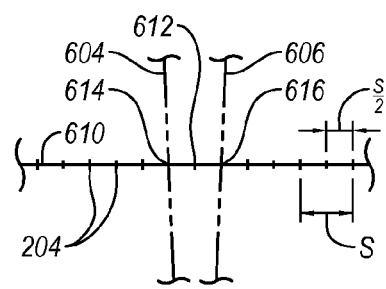
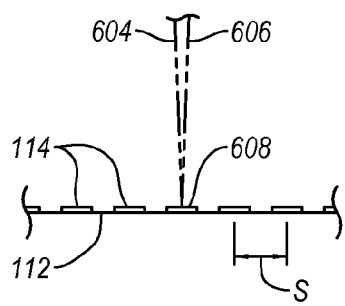
*Fig. 6A*

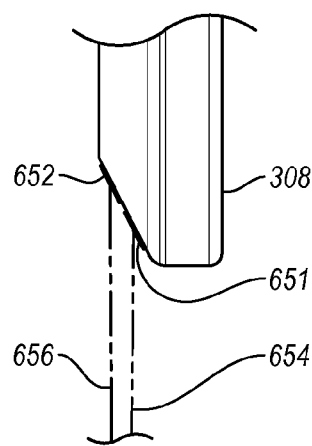
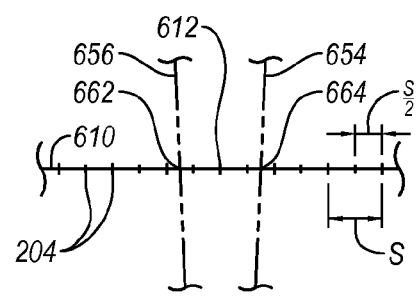
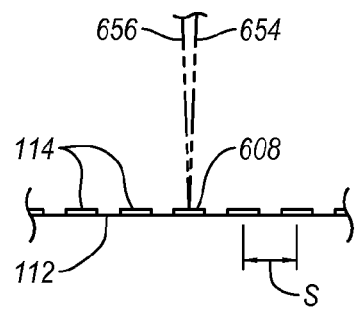
Fig. 6B

MULTILEVEL COMPUTED TOMOGRAPHY FOR RADIALLY-SHIFTED FOCAL SPOTS

BACKGROUND

Field

The embodiments discussed herein relate to computed tomography imaging systems.

Relevant Technology

Cone beam (CB) computed tomography (CT) involves the generation of volumetric image reconstruction of the internal structure of an object by collecting multiple projection images ("projections") in a single scan operation. Computed tomography is widely used in the medical field to view the internal structure of selected portions of the human body. Computed tomography is also used in the industrial and security fields to perform nondestructive inspection and to detect contraband and weapons in security screening.

Generally, multiple two-dimensional projections are made of an object. These two-dimensional projections are typically created by transmitting radiation from multiple positions through the object. The object absorbs some of the radiation based on the size and density of the object's internal structure. The unabsorbed radiation is collected by an imaging device, or imager, which typically includes an array of detectors. The two-dimensional projections may be generated using information about the relative attenuation of the radiation as collected by the imager. The collected two-dimensional projections may be used to generate a three-dimensional representation of the object using various tomographic reconstruction methods.

The quality of the three-dimensional representation of the object may depend on a number of factors. For example, the intensity of the radiation transmitted from the point source will affect the signal-to-noise ratio of the collected radiation. Furthermore, conventional algorithms for reconstructing the three-dimensional representation from the multiple two-dimensional projections may introduce inaccuracies to the representation, which are generally described as artifacts.

Conventionally, x-ray radiation is used in generating the two-dimensional projections of the object. Often, but not always, the x-rays are produced by an x-ray device rotating around the object. Generally, the x-ray devices contain a cathode that emits a flow of electrons that impinge material of a particular composition located at a target surface of an anode. As the electrons impinge the anode, x-rays and heat are produced. A beam of the resulting x-rays is directed toward the object and the imager. Increasing the flow of electrons that impinge the anode may increase the intensity of the resulting x-ray beam, but the heat produced is also increased.

Preferably, the temperature of the target surface, the anode, and/or other portions of the x-ray device are kept within a desired range to reduce the likelihood of heat-induced failure. The anode is often implemented as a disk spinning at high speeds. Generally, disk anodes absorb more heat without failure than stationary anodes. However, even with a disk anode, heat generated at the anode may act to limit the intensity of the x-ray beam.

The subject matter claimed herein is not limited to embodiments that solve any disadvantages or that operate only in environments such as those described above. Rather, this background is only provided to illustrate one exemplary technology area where some embodiments described herein may be practiced.

SUMMARY

Briefly summarized, embodiments described herein are directed to computed tomography (CT) imaging systems and methods for generating a volumetric image reconstruction of an object from multiple two-dimensional projections. In example embodiments, volumetric image reconstruction disclosed herein is described as multilevel reconstruction (MLR). Multilevel reconstruction may generate multiple levels of attenuation data defined relative to an examination region. The multiple levels may be determined using attenuation data collected from the multiple two-dimensional projections. Each level of the multiple levels may include attenuation data generated for an array of sample locations within the level. Furthermore, each sample location in the array of locations may include attenuation data for multiple projection angles. The attenuation data for the multiple projection angles and multiple sample locations of the multiple levels may then be convolved and backprojected to form a volumetric image reconstruction of the object. The multiple levels of attenuation data may improve the reconstruction, including increased resolution and reduced artifacts compared to conventional reconstruction.

The improved reconstruction resulting from the MLR may advantageously allow a focal spot to be radially shifted on an anode target surface such that the radially-shifted focal spots cover non-overlapping tracks on the anode target surface. Radially shifting the focal spot between non-overlapping tracks may allow the anode to safely handle higher heat generation, advantageously allowing the intensity of the x-ray beam to be increased and the volumetric image reconstruction to be further improved.

This Summary introduces a selection of concepts in a simplified form that are further described below in the Detailed Description. This Summary is not intended to identify key features or essential characteristics of the claimed subject matter, nor is it intended to be used as an aid in determining the scope of the claimed subject matter.

In one example embodiment, a method of volumetric image reconstruction of an examination region includes directing x-rays from an anode of an x-ray device towards the examination region from multiple positions relative to the examination region. The multiple positions relative to the examination region including multiple focal spot positions radially shifted relative to the anode. The method further includes detecting x-rays that have passed through the examination region and determining the first multiple x-ray attenuation values for each of the multiple positions. The first multiple x-ray values are based at least in part on the detected x-rays. The method further includes determining the second multiple x-ray attenuation values associated with multiple levels. At least one of the levels may intersect the examination region. The second multiple attenuation values are based at least in part on the first multiple attenuation values and the multiple positions. The method further includes generating a volumetric image reconstruction of the examination region based at least in part on the second multiple x-ray attenuation values.

In another example embodiment, a method of volumetric image reconstruction of an examination region includes collecting first multiple x-ray attenuation values. The method further includes collecting source data representing multiple positions relative to the examination region from which the collected first multiple attenuation values originated. The multiple positions relative to the examination region include multiple focal spot positions radially shifted relative to an anode of an x-ray device. Second multiple x-ray attenuation values are determined. The second multiple attenuation values are associated with multiple projection angles and multiple sample locations. The multiple sample locations are associated with multiple levels positioned relative to the examination region. For each projection angle of the multiple projection angles at each sample location of the multiple sample locations at each level of the multiple levels, an attenuation value is determined. The method further includes generating a volumetric image reconstruction of the examination region based at least in part on a backprojection of the second multiple attenuation values.

In yet another example embodiment, a CT imaging system includes a gantry, an x-ray device, and a detector array. The gantry is configured to rotate about an examination region. The x-ray device is mounted to the gantry such that the x-rays produced by the x-ray device are directed towards the examination region. The x-ray device includes a cathode, a rotatable anode, and a steering device. The cathode is configured to produce an electron stream. The rotatable anode includes a focal track configured to produce x-rays when struck by the electron stream at a focal spot. The steering device is configured to selectively steer the electron stream to strike multiple focal spot positions, including a first focal spot position and a second focal spot position such that the focal spot covers a first area of the focal track when the focal spot is at the first focal spot position and the focal spot covers a second area of the focal track when the focal spot is in the second focal spot position. The first focal spot position and the second focal spot position are positioned such that the first area and the second area do not overlap. The detector array is configured to detect x-rays that have passed through the examination region. The detector array includes multiple detectors arranged in rows and columns of detectors. A middle of a first detector is separated from the middle of an adjacent second detector by a detector distance. The CT imaging system is configured to produce x-rays from multiple x-ray device positions and the multiple focal spot positions. The CT imaging system is further configured to determine a first multiple x-ray attenuation values based at least in part on the x-rays detected by the detector array.

Additional features and advantages will be set forth in the description which follows, and in part will be obvious from the description, or may be learned by the practice of the embodiments. The features and advantages of the embodiments will be realized and obtained by means of the instruments and combinations particularly pointed out in the claims. These and other features will become more fully apparent from the following description and claims, or may be learned by the practice of the embodiments as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings in which:

FIG. 5A is a diagrammatic depiction of a front view of an examination region and a pair of x-ray beams that may be produced by the CT imaging system of FIG. 1;

FIG. 5B is a diagrammatic depiction of a side view of the examination region and the pair of x-ray beams of FIG. 5A;

FIG. 6A is a diagrammatic depiction of a front view of a pair of x-rays traveling from transversely-shifted focal spots, through a center level, and to a detector that may be implemented by the CT imaging system of FIG. 1;

FIG. 6B is a diagrammatic depiction of a side view of a pair of x-rays traveling from radially-shifted focal spots, through the center level, and to the detector of FIG. 6A;

DESCRIPTION OF EMBODIMENTS

Embodiments disclosed herein relate to computed tomography (CT) imaging systems and methods for performing volumetric image reconstruction of an examination region. Some embodiments disclose a volumetric image reconstruction described herein as multilevel reconstruction (MLR). Compared to conventional volumetric image reconstruction, MLR may generate a volumetric image reconstruction having improved resolution, improved isotropy throughout the examination region, and reduced artifacts while relatively minimally impacting processing requirements.

Advantageously, MLR may further accurately reconstruct the examination region from x-rays originating from multiple focal spot positions on a target track of an anode. In some embodiments, MLR may utilize all acquired x-rays in generating the volumetric image reconstruction, particularly x-rays at the edges of the x-ray beams in embodiments that employ multiple focal spot positions on the anode. Furthermore, MLR may advantageously use opposing projections in 360-degree reconstructions to provide full image reconstruction coverage.

Reference will now be made to the figures wherein like structures will be provided with like reference designations. The drawings are diagrammatic and schematic representations of exemplary embodiments and, accordingly, are not limiting of the scope of the claimed subject matter. The drawings are not necessarily drawn to scale and in some instances may be exaggerated to more clearly demonstrate the disclosed embodiments.

Figure 1:
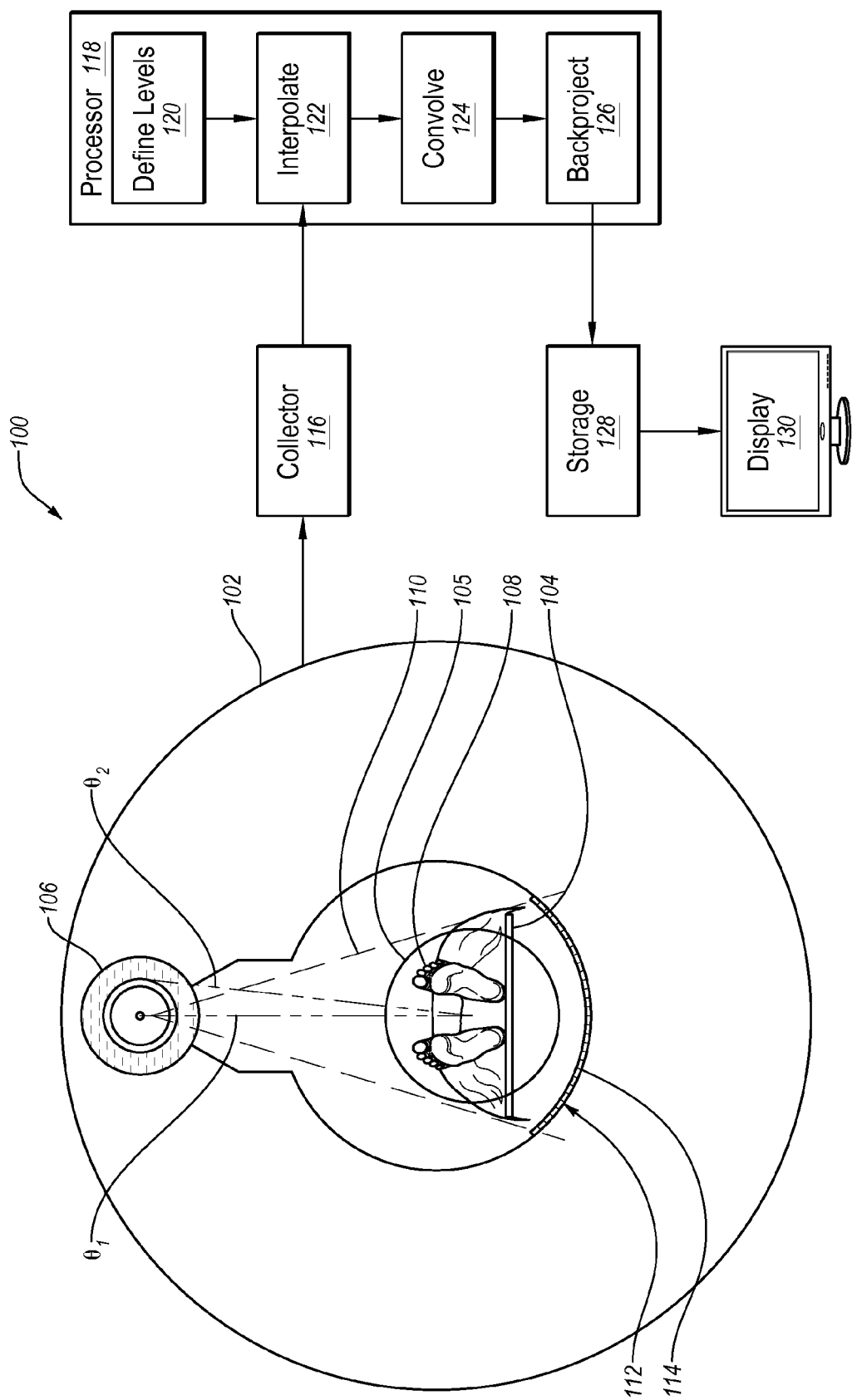
FIG. 1 is a depiction of an example computed tomography (CT) imaging system in which example embodiments may be employed.

FIG. 1 is a depiction of an example computed tomography (CT) scanner 100 in which example embodiments may be employed. Although FIG. 1 depicts a CT scanner 100 conventionally described as a third generation CT scanner, the embodiments described herein may be employed in other generations of CT scanners or in other imaging environments, provided suitable components are present and/or suitable imaging data may be acquired.

The CT scanner 100 generally comprises a rotatable gantry 102 and a platform 104. The platform 104 is generally positioned such that an object located on the platform 104 is located at least partially within an examination region 105. The examination region 105 is generally a volume for which a volumetric image reconstruction will be generated. Thus, a volumetric image reconstruction of objects within the examination region 105 will be generated. In many medically-related applications, the gantry 102 rotates about a patient 108 lying on the platform 104 at least partially within the examination region 105. The platform 104 and the patient 108 may move longitudinally, i.e., parallel to an axis of the gantry 102, as the gantry 102 rotates about the patient 108.

A radiation source such as an x-ray device 106 is mounted to the gantry 102. The x-ray device 106 is selectively energized during this rotation, thereby producing a diverging x-ray beam 110 that originates from the x-ray device 106. As the gantry 102 rotates, the position of the x-ray device 106 and the x-ray beam 110 changes. The position of the x-ray device 106 relative to the examination region 105 may be defined herein by a relative angular position θ. The x-ray beam 110 is generally directed towards the examination region 105 regardless of the relative angular position θ of the x-ray device 106. Although described as relative angles, a variety of other measurement techniques may be used to define the relative position of the x-ray device 106.

As shown in FIG. 1, the x-ray device 106 is positioned at $θ_1$. As the gantry 102 rotates, the x-ray device 106 may be positioned at $θ_2$. Similarly, the x-ray beam 110 may originate from the x-ray device 106 positioned at $θ_2$. Although only two relative angular positions—$θ_1$ and $θ_2$—are shown, the x-ray device 106 may produce x-rays at virtually any position relative to the examination region 105. For example, the x-ray device 106 may generate the x-ray beam 110 continuously as the gantry 102 is rotated. In addition to varying the position of the x-ray device 106 relative to the examination region 105, the location from which the x-ray beam 110 originates may also be varied relative to the x-ray device 106 during operation, as is described in further detail herein.

As the x-rays of the x-ray beam 110 pass through the patient 108 or other object, a portion of the x-rays are absorbed based on the relative size and density of the patient 108 encountered by the x-rays. After passing through the examination region 105, x-rays are received by a detector array 112. The detector array 112 may be made up of an array of radiation detectors 114 that receive the x-rays originating from the x-ray device 106. The detectors 114 convert the detected x-rays into electronic data. Generally, each detector 114 outputs a signal demonstrating the intensity of the x-rays received at each detector 114. The intensity of the x-rays received at each detector 114 generally indicates the degree of attenuation experienced by x-rays traveling through the object along a path defined from the origination position of the x-ray beam 110 to the individual detector 114. Thus, the term "attenuation values" as used herein may generally reference the relative intensity of the x-rays—detected or calculated—after passing through a portion of the examination region 105.

FIG. 1 shows a row of detectors 114 of the detector array 112. Although not shown, the detector array 112 includes additional rows of detectors 114 positioned behind and/or in front of the row of detectors 114 shown to form the detector array 112. For convenience, the detector array 112 is shown having fewer detectors 114 in a row than may typically be employed in the detector array 112. The detector array 112 may have many more detectors 114 than shown in FIG. 1. The embodiments described herein may be employed with conventional detector array 112 designs.

Spacing between adjacent detectors 114 is generally related to what is described herein as a resolution of the detector array 112. The spacing between detectors is generally the distance between a midline of a first detector and a midline of an adjacent second detector or an equivalent measurement. In some embodiments, the detector array 112 may have variable spacing. For example, the distance between adjacent detectors 114 may be larger for detectors 114 near edges of the detector array 112 than for a center of the detector array 112. In detector arrays 112 with variable spacing, the detector spacing may generally be based on the spacing between detectors 114 near the center of the detector array 112.

Although the detector array 112 is shown as a curved surface that travels with the gantry 102, embodiments described herein may be used with detector arrays having other shapes. In some embodiments, the detector array 112 may be a flat detector array that travels with the gantry 102. Alternately, the detector array 112 may have a circular shape and may remain stationary relative to the gantry 102. Alternately, the detector array 112 may have another shape suitable to receive x-rays that have passed through the examination region 105.

A collector 116 may collect electrical signals output by the detector array 112, along with corresponding information about the positions from which the x-ray beam 110 originated when producing the electrical signals. The origination location of the x-ray beam 110 may include the relative angular position θ of the x-ray beam 110 and/or the location from which the x-ray beam 110 originates relative to the x-ray device 106. The collector 116 may include a computer memory, computer storage, or the like.

A processor 118 may define multiple levels 120 associated with areas in or near the examination region 105. In some embodiments, the multiple levels may be defined such that at least one level intersects the examination region 105. As is described in additional detail herein, x-ray attenuation values for multiple sample locations within the levels and/or multiple projection angles at each sample location may be determined for and associated with the multiple levels. The multiple levels and the attenuation values associated with them are then used in reconstructing a volumetric image representation of the examination region 105 as described herein.

The processor 118 may determine the attenuation values for the multiple sample locations and the multiple projection angles within the multiple levels via interpolation 122 of the attenuation values detected at the detector array 112. The attenuation value determined for a particular projection angle at a particular sample location in a particular level may generally represent the relative attenuation an x-ray would experience traveling through the examination region 105 at the particular projection angle and passing through the particular sample location in the particular level. As described in detail herein, the interpolation 122 may be based at least in part on the attenuation values detected by the detector array 112, the relative angular position θ of the x-ray device 106 relative to the examination region 105, and/or the origination position of the x-ray beam 110 relative to the x-ray device 106.

The processor 118 may further convolve 124 the attenuation values associated with the multiple levels to prepare the attenuation values for backprojection. The convolved attenuation values associated with the multiple levels may be used, at least in part, to backproject 126 a volumetric image representation of the examination region 105. In some embodiments, voxels of the volumetric image reconstruction may further be based at least in part on an extrapolation of the reconstruction information associated with at least two of the multiple levels. The volumetric image representation of the examination region 105 may then be stored in storage 128 and/or displayed on a display 130.

Although shown as a single processor 118, the processor 118 may include multiple processors. For example, a task such as defining the multiple levels 120, interpolating 122, convolving 124, or backprojecting 126 may be performed over multiple processors, and/or one or more of the separate tasks may be performed by separate processors.

Figure 2:
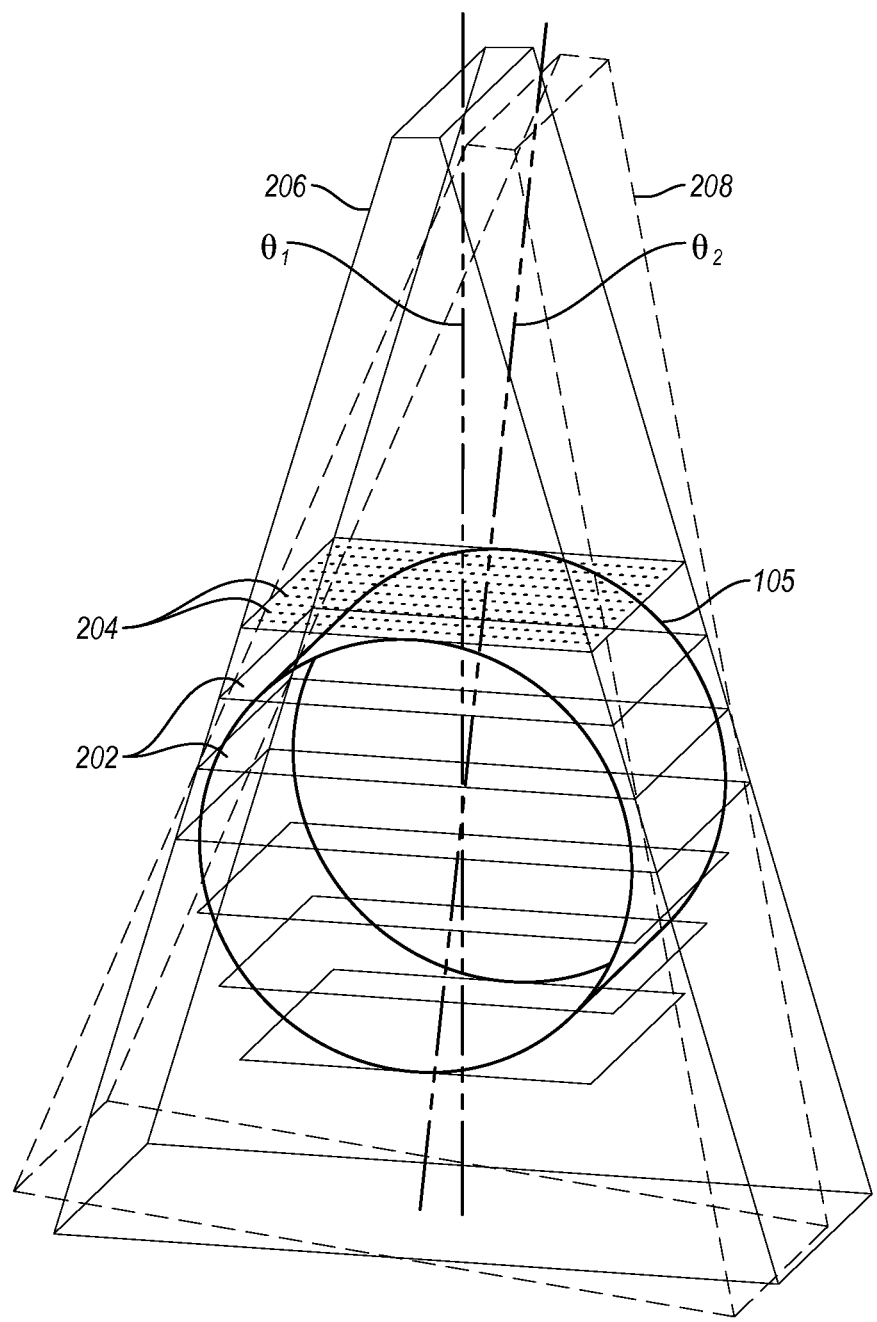
FIG. 2 is a diagrammatic depiction of an examination region relative to a pair of x-ray beams that may be produced by the CT imaging system of FIG. 1.

FIG. 2 is a diagrammatic depiction of the examination region 105 relative to a pair of x-ray beams 206 and 208 that may be produced by the CT scanner 100 of FIG. 1. A set of multiple levels 202 may be associated with the examination region 105. In some embodiments, a particular set of levels 202 may be defined for each x-ray beam 206 and 208. Generally, each set of levels 202 may be defined perpendicular to a nominal relative angular position θ of an associated x-ray beam. For example, the levels 202 shown in FIG. 2 may be defined as perpendicular to $\theta_1$ of the x-ray beam 206. A second set of levels (not shown) may be defined perpendicular to $\theta_2$ of the x-ray beam 208. Each level 202 may include multiple sample locations 204 within the level 202. Although only one level 202 is shown with sample locations 204 for convenience, each level 202 may include multiple sample locations 204. In some embodiments, seven levels 202 may be defined near and/or through the examination region 105 as shown in FIG. 2. However, more or fewer levels 202 may be defined. The levels 202 may be defined as being evenly spaced relative to the other levels 202. Alternately, the levels 202 may be unevenly spaced.

In some embodiments, the sample locations 204 may be arranged in an array having rows and columns of sample locations 204. The spacing of the sample locations 204 in the array may be defined relative to the spacing of the detectors 114 of the detector array 112 as discussed with reference to FIG. 1. For example, the spacing of the sample locations 204 may be equal to the spacing of the detectors 114. Such spacing gives each level 202 a sampling resolution equal to the resolution of the detector array 112. The sampling resolution of the levels 202 may be different from the resolution of the detector array 112. In some embodiments, the sampling resolution may be twice the resolution of the detector array 112, i.e., the spacing of the sample locations 204 may be half the detector 114 spacing of the detector array 112. In detector arrays 112 with variable detector spacing, in some embodiments, the sample location 204 spacing may generally be described relative to the detector 114 spacing near the center of the detector array 112. Although shown as an array, the sample locations 204 may be arranged in other suitable configurations. In some embodiments, the sample location 204 spacing may be variable within the level 202.

The sample locations 204 are generally locations at which attenuation values are associated. Each of the sample locations 204 may be associated with one or more attenuation values. The number and orientation of the attenuation values may be selected to allow suitable backprojection of the attenuation values associated with the multiple sample locations 204 and the multiple levels 202. Each individual attenuation value may generally represent a relative attenuation experienced by an x-ray traveling through the associated sample location 204 at a particular orientation.

With reference to FIGS. 1 and 2, the attenuation values associated with the sample locations 204 of the multiple levels 202 are generally determined from the attenuation values detected at the detector array 112, along with information about the locations at which the corresponding x-ray beams originated. As the gantry 102 rotates, x-rays are directed through the examination region 105 from varying locations. For example, x-ray beams 206 and 208 may originate at different relative angular positions $\theta_1$ and $\theta_2$. From these two relative angular positions, a number of attenuation values may be detected by the detector array 112. From the collected origination locations of the x-ray beams 206 and 208, the path each detected x-ray traveled through the examination region 105 may be determined. Furthermore, which levels 202 the detected x-rays intersected, as well as the locations and angle at which the detected x-ray intersected the levels 202 may be determined.

To determine attenuation values for the sample locations 204 and levels 202, the attenuation values from each origination location of the x-ray beams 206 and 208 may be considered. The attenuation values most closely approximating the desired sample locations 204 and orientations may be used to determine the attenuation values for the sample locations 204. If a particular detected x-ray is determined to have intersected a level at a particular sample location 204 with a particular orientation, the particular attenuation value associated with the detected x-ray may be associated with the particular sample location 204 and orientation. Generally, attenuation values may be determined for each projection angle and sample location 204 by interpolating appropriate attenuation values detected at the detector array 112.

In operation, x-ray beams are generally directed at the examination region 105 from many more than two origination locations. In some embodiments, the x-ray beams may be directed at the examination region 105 from opposing positions, i.e., from a first relative angular position of the gantry and a second relative angular position one-hundred-eighty (180) degrees from the first. Advantageously, attenuation values from opposing projections may be accurately used to generate the attenuation values for the multiple sample locations 204 and projection angles. When the attenuation values have been determined for the multiple sample locations 204, projection angles and levels 202, the attenuation values may be convolved and backprojected to generate a volumetric image reconstruction of the examination region 105.

Advantageously, the accuracy of the volumetric image reconstruction resulting from the use of MLR may permit an accurate reconstruction to be obtained even when a focal spot on an anode is radially shifted to a degree that allows non-overlapping tracks to be formed on the anode. Conventional methods of reconstruction may not generate a volumetric image reconstruction accurately enough to permit the focal spot to be radially shifted to a degree that allows non-overlapping tracks to be formed on the anode. However, employing MLR may provide benefits without radially shifting focal spots.

Figure 3:
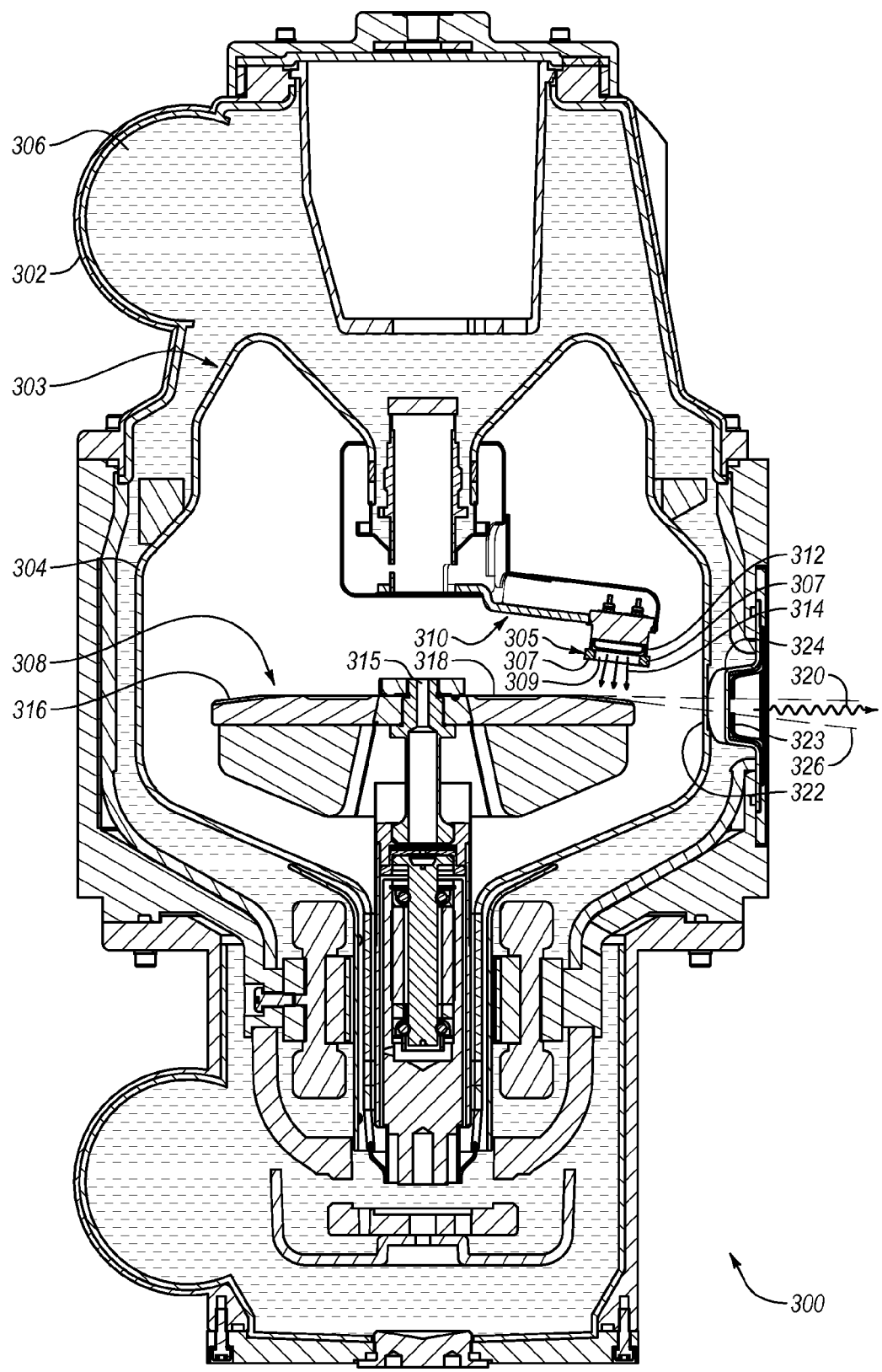
FIG. 3 is a simplified cutaway side view of an example x-ray device that may be included in the CT imaging system of FIG. 1.

FIG. 3 is a simplified cutaway side view of an example x-ray device 300 that may generally correspond to the x-ray device 106 of FIG. 1. The x-ray device 300 may be configured to radially shift the focal spot on an anode 308 to form non-overlapping tracks. The x-ray device 300 may be further configured to transversely shift the focal spot on the anode 308. Shifting the focal spot to multiple locations on the anode 308 may provide increased attenuation data to ultimately improve the volumetric image reconstruction. Furthermore, radially shifting the focal spot to cover non-overlapping tracks on the anode 308 may allow the anode 308 and the x-ray device 300 to handle higher heat generation.

As a result, the x-ray device 300 may generally increase the intensity of an x-ray beam 326 generated by the x-ray device 300. Increasing the intensity of the x-ray beam 326 may further improve the quality of attenuation data collected by a CT imaging device and may improve the quality of the resulting volumetric image reconstruction. For example, increasing the intensity of the x-ray beam 326 may generally improve a signal-to-noise ratio of the attenuation data.

The x-ray device 300 includes an x-ray tube 303 having a vacuum enclosure 304. A fluid coolant 306 may also be positioned within the outer housing 302 to circulate around the vacuum enclosure 304 to assist in x-ray device 300 cooling and to provide electrical isolation between the vacuum enclosure 304 and the outer housing 302. In one embodiment, the fluid coolant 306 comprises dielectric oil, which exhibits acceptable thermal and electrical insulating properties.

A rotating anode 308 and a cathode 310 are positioned within the vacuum enclosure 304. The anode 308 is spaced apart from and oppositely positioned to the cathode 310. Generally, the anode 308 is at least partially composed of a thermally conductive material. In some embodiments, the anode 308 is at least partially composed of tungsten or a molybdenum alloy. The anode 308 and the cathode 310 are connected within an electrical circuit that allows for the application of a high-voltage potential between the anode 308 and the cathode 310.

The cathode 310 includes a filament 312 that is connected to an appropriate power source. During operation of the x-ray device 300, an electrical current is passed through the filament 312 to cause electrons, designated at 314, to be emitted from the cathode 310 by thermionic emission. The application of a high-voltage differential between the anode 308 and the cathode 310 causes the electrons 314 to accelerate from the filament 312 toward a focal track 316 positioned on a target surface 318 of the anode 308. The focal track 316 is typically composed of tungsten or a similar material having a high atomic ("high Z") number. As the electrons 314 accelerate, they gain a substantial amount of kinetic energy, and upon striking the target material on the focal track 316, some of this kinetic energy is converted into electromagnetic waves of very high frequency, i.e., x-rays 320.

The focal track 316 and the target surface 318 are oriented so that emitted x-rays 320 are directed toward a vacuum enclosure window 322. The vacuum enclosure window 322 is comprised of an x-ray transmissive material and is positioned along a wall of the vacuum enclosure 304 at a location that is aligned with the focal track 316. An x-ray transmissive window 324 and a collimator 323 attached to the outer housing 302 may be spaced apart from and oppositely positioned to the vacuum enclosure window 322 as generally disclosed in FIG. 3. The collimator 323 may stop all but a desired portion of the emitted x-rays 320 from exiting the outer housing 302. The x-rays 320 that do pass through the collimator 323 may substantially form a diverging x-ray beam 326.

A steering mechanism 305 may be positioned proximate to the path of the electrons 314. The steering mechanism 305 may allow the path of the electrons 314 to be altered such that the location (described herein as a focal spot) where the electrons 314 strike the focal track 316 may be selectively altered. The steering mechanism 305 includes a pair of steering devices 307 and in some embodiments, another pair of steering devices 309 (only one-half of the pair of steering devices 309 is shown in FIG. 3). The steering devices 307 and 309 may include electromagnetic devices that may be operated to alter the path of the electrons 314. However, the steering devices 307 and 309 may include electrostatic devices or the like.

As shown in FIG. 3, the pair of steering devices 307 may be positioned to radially shift the path of the electrons 314—and the focal spot—relative to the anode 308. Radially shifting the focal spot relative to the anode 308 as described herein generally includes moving the focal spot primarily toward or away from an axis 315 of the anode 308. The other pair of steering devices 309 may be positioned to transversely shift the path of the electrons 314—and the focal spot—relative to the anode 308. Transversely shifting the focal spot relative to the anode 308 as described herein generally includes moving the focal spot primarily tangentially relative to the axis 315 of the anode 308.

In some embodiments, the steering mechanism 305 may be controlled via square-wave signals to cause the steering devices 307 and 309 to shift the focal spot between four focal spot locations. In some embodiments, the focal spot locations may move in a quad focal spot pattern. The focal spot may be radially shifted by a distance such that the relative radial positions of the focal spots follow non-overlapping tracks along the focal track 316 of the anode 308, as may be disclosed with reference to FIG. 4.

Figure 4:
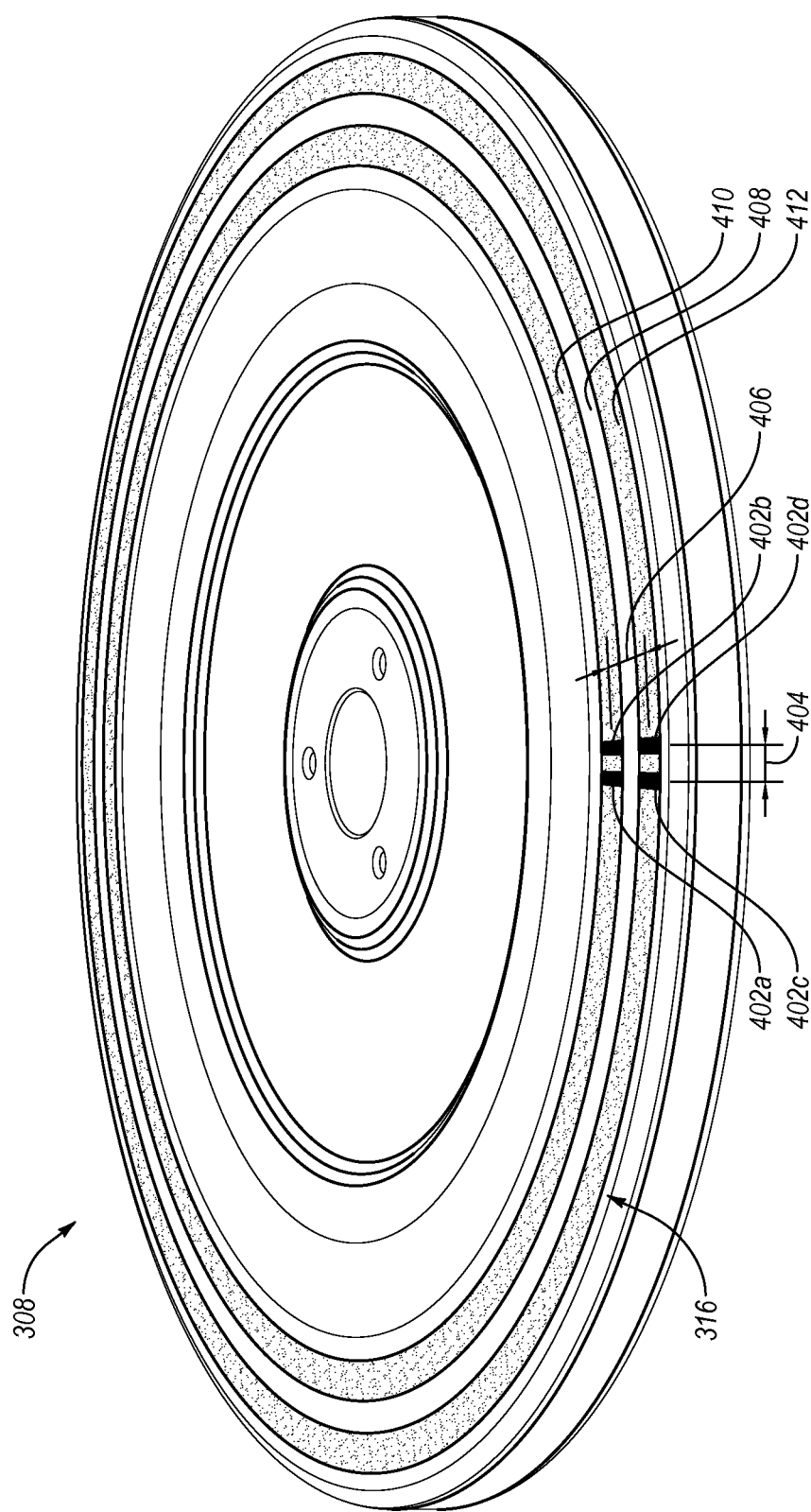
FIG. 4 is a perspective view of an anode that may be included in the x-ray device of FIG. 3.

FIG. 4 illustrates the anode 308 of FIG. 3 including multiple focal spot locations 402a, 402b, 402c, and 402d (collectively "focal spot locations 402"). By operating the steering mechanism 305 of FIG. 3, the focal spot may be shifted radially 406 and, optionally, may also be shifted transversely 404. In some embodiments, signals may be sent to the steering device such that the focal spot moves between focal spot locations 402 in a desired pattern.

The focal spot locations 402 may be positioned such that non-overlapping tracks are formed. For example, as the anode 308 spins, a track 410 may be followed by the focal spot in locations 402a and 402b. A track 412 may also be followed by the focal spot in locations 402c and 402d. The focal spots 402 may be positioned such that tracks 410 and 412 do not overlap. Similar tracks 410 and 412 may be formed when the focal spot is shifted only radially 406. The lack of overlap between the tracks 410 and 412 may improve the heat rating of the anode 308. In some embodiments, a gap 408 between the tracks 410 and 412 may improve the heat rating of the anode 308 further. For example, the gap 408 may reduce conductive heat transfer between the tracks 410 and 412. In some embodiments, shifting the focal spot as described herein may provide some of the benefits described herein even when MLR is not performed.

By forming tracks 410 and 412 that do not overlap, no single area of the anode 308 is constantly being impacted by electrons the entire time the x-ray device 300 is emitting an x-ray beam 326. When the focal spot is in the focal spot locations 402a and 402b, the anode heats up along the portion(s) of track 410 that the focal spot covers. When the focal spot is in the focal spot locations 402c and 402d, the anode heats up along the portions(s) of track 412 that the focal spot covers. However, when the focal spot is in the focal spot locations 402c and 402d, the heated portion(s) of track 410 are allowed to dissipate heat. Similarly, when the focal spot is in the focal spot locations 402a and 402b, the heated portion(s) of track 412 are allowed to dissipate heat.

As a result, the heat that may be absorbed by the anode 308 and its accompanying x-ray device 300 may be increased.

Furthermore, shifting the focal spot between the focal spot locations 402, additional attenuation data is generally acquired, as the rays originating at the different focal spot locations 402 travel different paths through the examination region 105. Thus, the resolution of the volumetric image reconstruction may be improved, artifacts may be reduced, and the like. In some embodiments, the focal spot may be radially shifted 406 such that x-rays detected from the radially-shifted focal spots are longitudinally interleaved proximate a center of the examination region by one-and-a-half times the detector 114 spacing as described with reference to FIG. 1. Such a radial shifting distance may promote non-overlapping tracks 410 and 412 and further promotes a generally even x-ray coverage of the examination region 105 at the middle of a center level 202 as described with reference to FIG. 2. In some embodiments, the focal spot may be transversely shifted 404 such that x-rays detected from the transversely-shifted focal spots transversely interleaved proximate a center of the examination region by one-half the detector 114 spacing as described with reference to FIG. 1.

FIG. 5A is a diagrammatic depiction of a front view of an examination region and a pair of x-ray beams that may be produced by the CT imaging system of FIG. 1. Shifting the focal spots on the focal track 316 of the anode 308 relative to the collimator 323 may cause the shape of the x-ray beam to change. FIG. 5B is a diagrammatic depiction of a side view of FIG. 5A. When the focal spot is at focal spot location 501, x-ray beam 502 may result. When the focal spot is at focal spot location 503—relatively closer to the axis 315 of the anode 308 and relatively farther away from the collimator 323 than the focal spot 501—x-ray beam 504 may result. As a result of the differently-shaped x-ray beams 502 and 504, a space 506 may be formed that is covered by fewer than all of the x-ray beams 502 and 504. A portion of the examination region 105 may fall within the space 506. In some embodiments, the examination region 105 may be within all of the x-ray beams 502 and 504, but one or more levels 202 (shown in FIG. 2) may extend into the space 506. X-rays at the edges of the x-ray beams 502 and 504 may be used in interpolating attenuation values for any sample points located in the space 506. Advantageously, using x-rays at the edges of the x-ray beams 502 and 504 to determine the attenuation values for the multiple levels may allow more accurate attenuation values to be determined while minimizing the dose of unused x-rays delivered to a patient 108 (shown in FIG. 1) in the examination region 105.

Although the focal spot locations 501 and 503 are shown as being radially shifted, the shape of the x-ray beam may be similarly changed, albeit to a potentially lesser degree, when the focal spot is transversely shifted. In some embodiments, an analogous interpolation may be performed between the x-ray beams that result from transversely-shifted focal spot locations.

FIG. 6A is a diagrammatic depiction of a front view of a pair of x-rays 604 and 606 traveling from transversely-shifted focal spot locations 601 and 602, through a center level 610 and to a detector 608 that may be implemented by the CT scanner 100 of FIG. 1. The figure is not drawn to scale. For clarity, the center level 610 and the detector array 112 are depicted at a relatively larger scale than the anode 308. The center level 610 generally corresponds to the center level of the levels 202 as described with reference to FIG. 2. Furthermore, only the x-rays 604 and 606 detected by the center detector 608 of the detector array 112 are shown for convenience. In operation, x-rays originating from each focal spot location 601 and 602 are detected at each detector 114 of the detector array 112.

In some embodiments, the transversely-shifted focal spot locations 601 and 602 are selected such that the x-rays 604 and 606 intersect the center level 610 at sample locations 614 and 616 located a one-half sample distance (depicted as S/2) away from a center sample location 612. The half sample distance S/2 may be one-half the detector 114 spacing (depicted as S). Such spacing may cause the x-rays produced at the focal spot locations 601 and 602 to be interleaved by a one-half sample S/2 proximate the center sample location 612 of the center level 610 of an examination region 105 (shown in FIG. 2).

FIG. 6B is a diagrammatic depiction of a side view of a pair of x-rays 654 and 656 traveling from radially-shifted focal spot locations 651 and 652, through the center level 610 and to the detector 608 of FIG. 6A. Similar to FIG. 6A, only the x-rays 654 and 656 detected by the center detector 608 of the detector array 112 originating from radially-shifted focal spot locations 651 and 652 are shown for convenience. In operation, x-rays originating from the radially-shifted focal spot locations 651 and 652 are detected at each detector 114 of the detector array 112.

In some embodiments, the radially-shifted focal spot locations 651 and 652 are selected such that the x-rays 654 and 656 intersect the center level 610 at locations 662 and 664 located three-fourths (¾) of a sample distance S away from a center sample location 612. Such spacing may cause the x-rays produced at the focal spot locations 651 and 652 to be interleaved by one-and-a-half samples proximate the center sample location 612 of the center level 610 of an examination region 105 (shown in FIG. 2).

Determining attenuation values at each sample location 204 for each projection angle may be performed via interpolation of detected attenuation values determined to intersect the appropriate level 202 (shown in FIG. 2) near the sample locations 204 and projection angles. In some embodiments, a two-step interpolation process may be employed. The first step of the interpolation process may be described herein with reference to FIG. 7A and the second step may be described with reference to FIG. 7B.

The first step of the interpolation process may include a fan-to-parallel interpolation for each column of sample locations 204. However, parallel rays are not required to perform the MLR. In embodiments that employ non-parallel rays, another interpolation may be used.

Figure 7A:
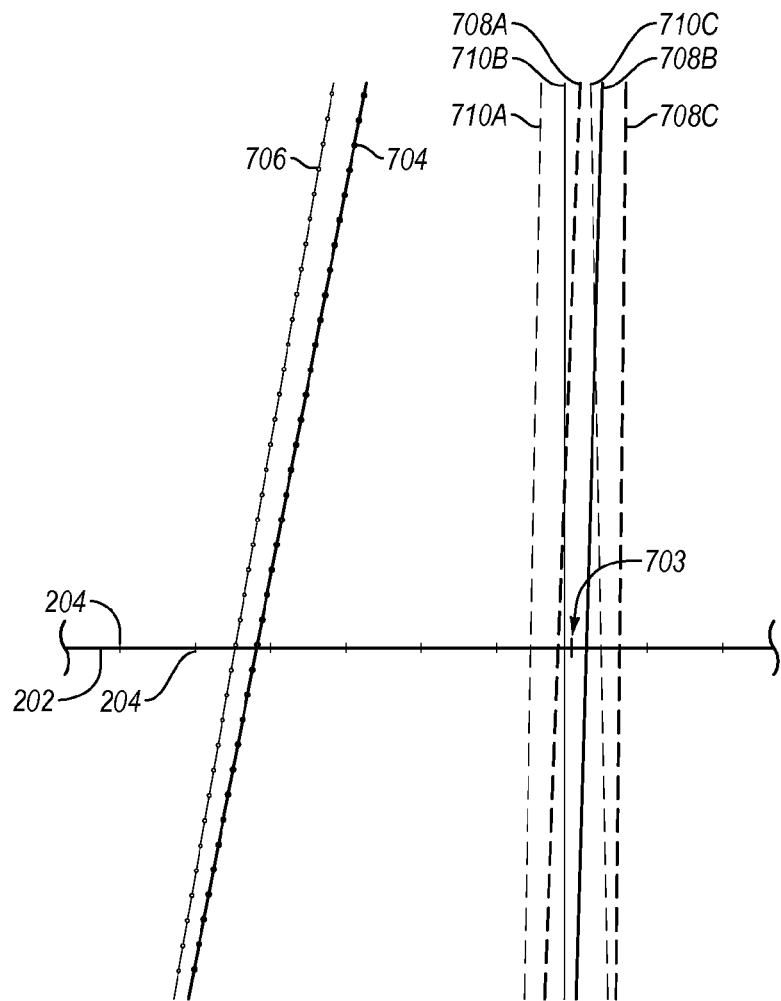
FIG. 7A is a diagrammatic depiction of a front view of a portion of a level intersected by a number of x-rays that may be produced by the CT imaging system of FIG. 1.
Figure 7B:
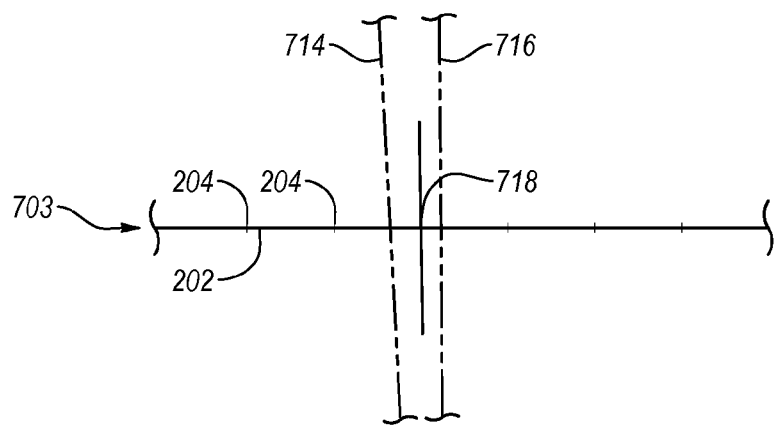
FIG. 7B is a diagrammatic depiction of a side view of the portion of the level of FIG. 7A intersected by a pair of interpolated x-rays.

FIG. 7A is a diagrammatic depiction of a front view of a portion of a level 202 intersected by a number of fans of x-rays 708A, 708B, 708C (collectively "fans of x-rays 708"), 710A, 710B, and 710C (collectively "fans of x-rays 710") that may be produced by the x-ray device 106 and detected by columns of detectors 114 of FIG. 1. The fans of x-rays 708 may be produced at a relative angular position 704 of the x-ray device 106. Similarly, the fans of x-rays 710 may be produced at a relative angular position 706 of an x-ray device 106. The relative angular positions 704 and 706 generally correspond to the relative angular position θ described with reference to FIG. 1. Many more fans of x-rays may be detected from each of the relative angular positions 704 and 706. Furthermore, fans of x-rays may be produced at many more relative angular positions.

A fan-to-parallel interpolation may be performed for an example sample location column 703. In some embodiments, the x-rays originating from the relative angular positions 704 and 706 positioned closest to perpendicular with the sample location column 703 may be considered.

From the relative angular positions 704 and 706, attenuation data associated with the fans of x-rays 708B and 710B that most closely straddle the sample location column 703 may be interpolated to determine a column of attenuation values. In some embodiments, the closest fans of x-rays 708B and 710B may be interpolated using a weighted average based on the respective distance and/or respective angular distance from the sample location column 703. The interpolation may be performed for the entire sample location column 703, and for each column of sample locations 204 at each level 202.

In the second step, the attenuation data interpolated at the first step may be further interpolated to intersect the sample location column 703 at the sample points 204. The interpolated attenuation value 718 may be oriented consistent with the wedge shape formed by the x-ray beam. In some embodiments, the interpolated attenuation value 718 may be determined by interpolating the two closest attenuation values 714 and 716 using a weighted average based on the respective distance from the particular sample location intersected by the desired interpolated attenuation value 718. This interpolation may be repeated for each sample location 204 in each level 202.

When the attenuation values have been determined for each sample location 204 and projection angle for each level, convolution may be performed. The convolved attenuation data may further be backprojected to generate a volumetric image reconstruction. In some embodiments, a particular voxel of the volumetric image reconstruction is interpolated based on the voxel's relative position between levels 202.

Figure 8B:
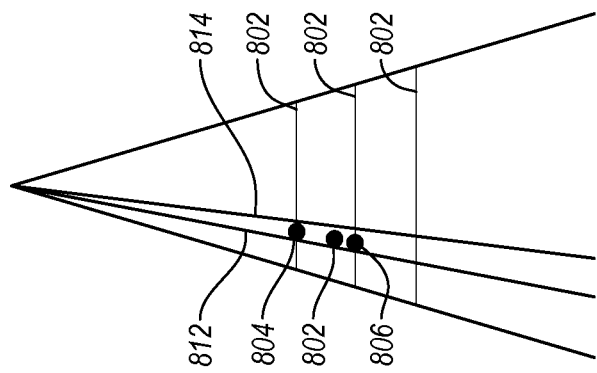
FIG. 8B is a side view of the volumetric reconstruction of the voxel of FIG. 8A.
Figure 8A:
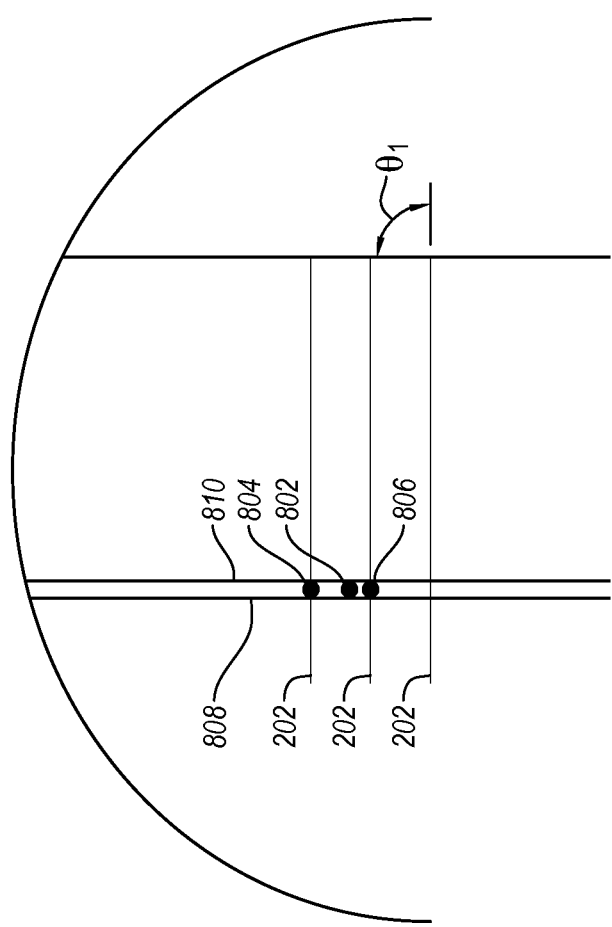
FIG. 8A is a diagrammatic depiction of a front view of a volumetric reconstruction of a voxel located between levels that may be produced by the CT imaging system of FIG. 1.

FIG. 8A is a diagrammatic depiction of a front view of a volumetric reconstruction of a voxel 802 located between levels 202. FIG. 8B is a diagrammatic depiction of a side view of the volumetric reconstruction of the voxel 802 located between the levels 202. The levels 202 may be associated with a relative angular position $\theta_1$. In some embodiments, a backprojection value for the voxel 802 is obtained by interpolating backprojection values 804 and 806 obtained at levels 202 adjacent the voxel 802. The backprojection values 804 and 806 may be calculated via two-dimensional interpolation of the backprojection values corresponding to adjacent rays, such as rays 808, 810, 812, and 814.

Advantageously, generating a volumetric image reconstruction via MLR may significantly improve the accuracy of the reconstructions compared to conventional reconstruction techniques. Furthermore, the significantly improved accuracy may be accomplished by introducing only a relatively minor increase in processing using MLR as described herein. For example, processing related to convolving the attenuation values may increase linearly in relation to the number of levels 202 defined in the MLR. However, processing related to backprojection may be minimally impacted in the MLR. Because processing resources used in backprojection are generally much higher than in convolution, overall MLR processing experiences a relatively minor increase compared to conventional reconstruction.

Figure 9:
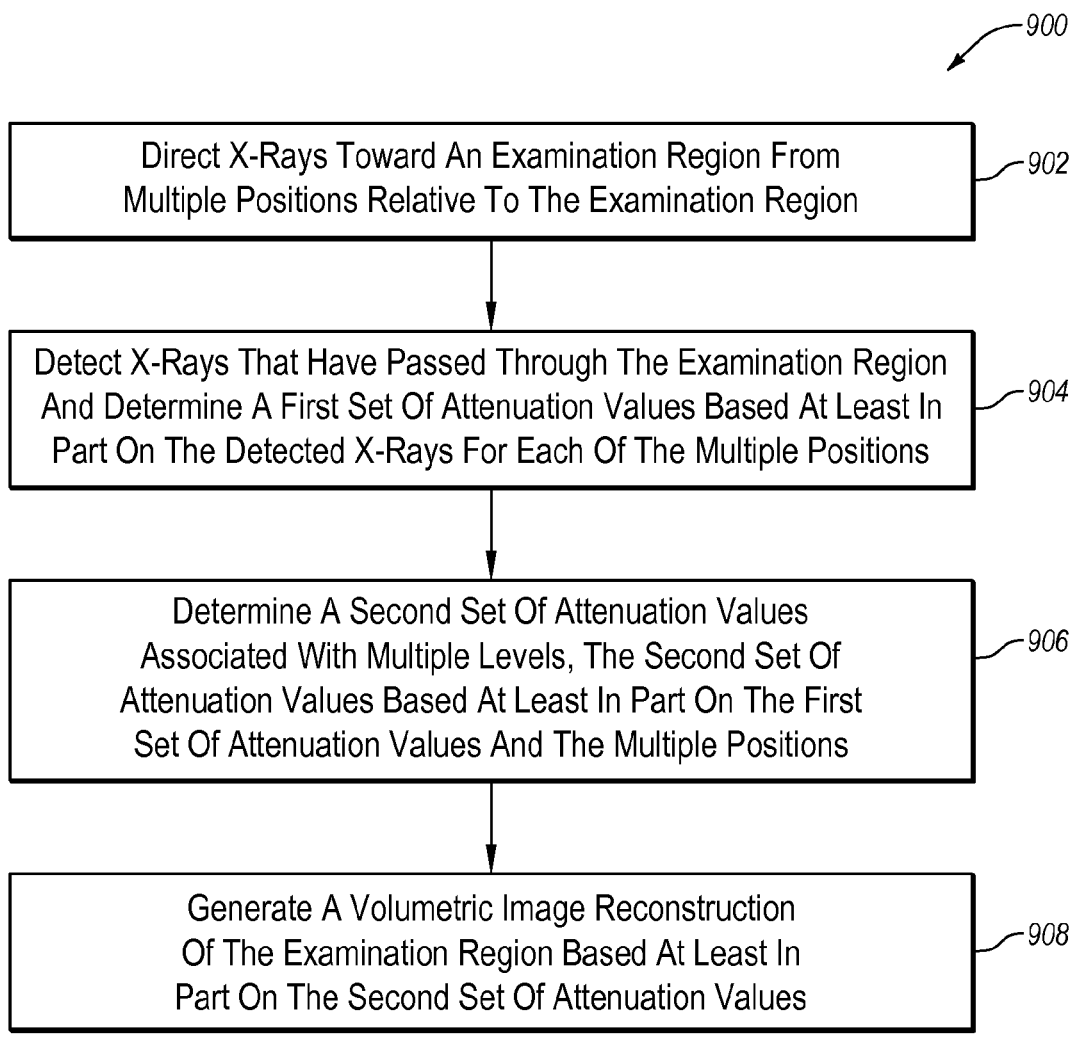
FIG. 9 is a flowchart of an example method of volumetric image reconstruction of an examination region.

FIG. 9 is a flowchart of an example method 900 of volumetric image reconstruction of an examination region. The method 900 may be implemented, in some embodiments, by a CT imaging system generally corresponding to the CT scanner 100 of FIG. 1. Although the method 900 is illustrated as discrete blocks, various blocks may be divided into additional blocks, combined into fewer blocks, or eliminated, depending on the desired implementation.

The method 900 may begin at block 902, in which x-rays are directed towards an examination region from multiple positions relative to the examination region. In some embodiments, the multiple positions include multiple locations of an x-ray device relative to the examination region. Alternately or additionally, the x-ray device may include a rotatable anode, and the multiple positions relative to the examination region may further include multiple focal spot locations on the anode.

The multiple focal spot locations on the anode may include two or more focal spots transversely shifted relative to the anode. The transversely-shifted multiple focal spot locations on the anode may be transversely shifted. Such x-rays detected from the transversely-shifted focal spots are transversely interleaved proximate a center of the examination region by half a detector spacing. The detector spacing may be equivalent to the distance between midlines of adjacent detectors of a detector array configured to detect the x-rays.

Alternately or additionally, the multiple focal spot locations on the anode may include two or more focal spots radially shifted relative to the anode. The radially-shifted multiple focal spot locations on the anode may be radially shifted. Such x-rays detected from the radially-shifted focal spots are longitudinally interleaved proximate a center of the examination region by one-and-a-half times the detector spacing. Alternately or additionally, the radially-shifted focal spots may be radially shifted between a first radial position and a second radial position on the anode such that an area of the anode covered by the focal spot in the first radial position does not overlap an area of the anode covered by the focal spot in the second radial position.

In block 904, x-rays that have passed through the examination region are detected and a first set of attenuation values based at least in part on the detected x-rays is determined for each of the multiple positions.

In block 906, a second set of attenuation values is determined. The second set of attenuation values is associated with multiple levels. At least one of the multiple levels intersects the examination region. The second set of attenuation values is based at least in part on the first set of attenuation values and the multiple positions. In some embodiments, the second set of attenuation values are further associated with multiple projection angles relative to the examination region. Alternately or additionally, the second set of attenuation values may be further associated with an array of sample locations within each level of the multiple levels. In some embodiments, the distance between adjacent sample locations may be equal to half a distance between adjacent detectors of a detector array configured to detect the x-rays.

In some embodiments, the second set of attenuation values associated with the multiple levels includes interpolating two or more fans of x-rays in a transverse direction to determine a transversely interpolated fan of x-rays intersecting a line in which a column of the sample locations is located. The transversely interpolated fan of x-rays may also be interpolated in a longitudinal direction such that the longitudinally interpolated x-rays intersect the column at each of the sample locations of the column.

In block 908, a volumetric image reconstruction of the examination region is generated at least in part on the second set of attenuation values. In some embodiments, the volumetric image reconstruction is performed by backprojecting the second set of attenuation values. In some embodiments, a voxel of the reconstruction may be determined at least in part by interpolating two or more voxels located at two or more levels.

The embodiments described herein may include the use of a special purpose or general purpose computer including various computer hardware or software modules, as discussed in greater detail below.

Embodiments described herein may be implemented using computer-readable media for carrying or having computer-executable instructions or data structures stored thereon. Such computer-readable media may be any available media that may be accessed by a general purpose or special purpose computer. By way of example, and not limitation, such computer-readable media may include tangible computer-readable storage media including random-access memory (RAM), read-only memory (ROM), electrically erasable programmable read-only memory (EEPROM), compact disc read-only memory (CD-ROM) or other optical disk storage, magnetic disk storage or other magnetic storage devices, or any other storage medium which may be used to carry or store desired program code in the form of computer-executable instructions or data structures and which may be accessed by a general purpose or special purpose computer. Combinations of the above may also be included within the scope of computer-readable media.

Computer-executable instructions include, for example, instructions and data which cause a general purpose computer, special purpose computer, or special purpose processing device to perform a certain function or group of functions. Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

As used herein, the term "module" or "component" may refer to software objects or routines that execute on the computing system. The different components, modules, engines, and services described herein may be implemented as objects or processes that execute on the computing system (e.g., as separate threads). While the system and methods described herein are preferably implemented in software, implementations in hardware or a combination of software and hardware are also possible and contemplated. In this description, a "computing entity" may be any computing system as previously defined herein, or any module or combination of modulates running on a computing system.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A method of volumetric image reconstruction of an examination region, the method comprising:
    directing x-rays from an anode of an x-ray device towards the examination region from a plurality of positions relative to the examination region, the plurality of positions relative to the examination region including a plurality of focal spot positions radially shifted relative to the anode, wherein the plurality of positions relative to the examination region further include a plurality of x-ray device positions relative to the examination region:
        (i) detecting x-rays that have passed through the examination region; and
        (ii) determining a first plurality of x-ray attenuation values, the first plurality of attenuation values based at least in part on the detected x-rays;
    determining a second plurality of x-ray attenuation values, the second plurality of attenuation values associated with a plurality of levels, wherein the plurality of levels are spaced along the x-rays with respect to the radially shifted focal spot positions and at least one of the plurality of levels intersecting the examination region, the second plurality of attenuation values based at least in part on the first plurality of attenuation values and the plurality of positions; and
    generating a volumetric image reconstruction of the examination region based at least in part on the second plurality of attenuation values associated with the plurality of levels.

2. The method of claim 1, wherein the second plurality of attenuation values is further associated with an array of sample locations within each level of the plurality of levels.

3. The method of claim 2, wherein the sample locations are spaced by a sample distance equal to half a detector distance, the detector distance equivalent to the distance between midlines of adjacent detectors of a detector array configured to detect the x-rays.

4. The method of claim 2, wherein determining the second plurality of attenuation values associated with the plurality of levels includes interpolating two or more fans of x-rays in a transverse direction to determine a transversely interpolated fan of x-rays intersecting a line in which a column of the sample locations is located.

5. The method of claim 4, wherein determining the second plurality of attenuation values includes interpolating the x-rays of the transversely interpolated fan of x-rays in a longitudinal direction such that the longitudinally interpolated x-rays intersect the column at each of the sample locations of the column.

6. The method of claim 1, wherein the plurality of levels includes a plurality of subsets of levels, wherein each subset of levels is associated with a different x-ray device position of the plurality of x-ray device positions relative to the examination region.

7. The method of claim 1, wherein the plurality of focal spot positions transversely shifted relative to the anode are transversely shifted such that the x-rays detected from the focal spot positions transversely shifted relative to the anode are transversely interleaved proximate a center of the examination region by half a detector spacing, the detector spacing equal to the distance between midlines of adjacent detectors of a detector array configured to detect the x-rays.

8. The method of claim 1, wherein the plurality of focal spot positions radially shifted relative to the anode are radially shifted such that the x-rays detected from the focal spot positions radially shifted relative to the anode are longitudinally interleaved proximate a center of the examination region by one-and-a-half times a detector spacing, the detector spacing equal to the distance between midlines of adjacent detectors of a detector array configured to detect the x-rays.

9. The method of claim 1, wherein the focal spot positions radially shifted relative to the anode include a first radial position and a second radial position on the anode such that an area of the anode covered by the focal spot in the first radial position does not overlap an area of the anode covered by the focal spot in the second radial position.

10. The method of claim 1, wherein the plurality of positions relative to the examination region further includes a plurality of focal spot positions transversely shifted relative to the anode.

11. The method of claim 1, wherein generating the volumetric image reconstruction of the examination region based at least in part on the second plurality of attenuation values includes interpolating a voxel based on a position of the voxel with respect to projection angles in a transverse and longitudinal direction, and with respect to the position of the voxel relative to the levels.

12. A method of volumetric image reconstruction of an examination region, the method comprising:
   collecting a first plurality of x-ray attenuation values;
   collecting source data representing a plurality of positions relative to the examination region from which the collected first plurality of attenuation values originated, the plurality of positions relative to the examination region including a plurality of focal spot positions radially shifted relative to an anode of an x-ray device wherein the plurality of positions relative to the examination region further includes a plurality of x-ray device positions relative to the examination region, and wherein the plurality of positions relative to the examination region further includes a plurality of focal spot positions transversely shifted relative to the anode;
   determining a second plurality of x-ray attenuation values, the second plurality of x-ray attenuation values associated with a plurality of sample locations, the plurality of sample locations associated with a plurality of levels, the plurality of levels positioned relative to the examination region and spaced with respect to the radially shifted focal spot positions, determining the second plurality of attenuation values including determining an attenuation value for each sample location of the plurality of sample locations at each level of the plurality of levels; and
   generating a volumetric image reconstruction of the examination region based at least in part on a back-projection of the second plurality of attenuation values associated with the plurality of levels.

13. The method of claim 12, wherein the plurality of levels includes a plurality of subsets of levels, wherein each subset of levels is associated with a different x-ray device position of the plurality of x-ray device positions relative to the examination region.

14. The method of claim 12, wherein the plurality of focal spot positions radially shifted relative to the anode includes a first radial focal spot position and a second radial focal spot position on the anode such that an area of the anode covered by a focal spot in the first radial focal spot position does not overlap an area of the anode covered by the focal spot in the second radial focal spot position.

15. A computed tomography (CT) imaging system comprising:
   a gantry configured to rotate about an examination region;
   an x-ray device mounted to the gantry such that x-rays produced by the x-ray device are directed towards the examination region, the x-ray device including:
      a cathode configured to produce an electron stream,
      a rotatable anode including a focal track configured to produce x-rays when struck by the electron stream at a focal spot, and
      a steering device configured to selectively steer the electron stream to strike a plurality of focal spot positions on the focal track, including a first focal spot position and a second focal spot position such that the focal spot covers a first area of the focal track when the focal spot is at the first focal spot position and the focal spot covers a second area of the focal track when the focal spot is in the second focal spot position, wherein the plurality of focal spot positions on the focal track further include a plurality of x-ray device positions relative to the examination region; and
   a detector array configured to detect the x-rays that have passed through the examination region, the detector array including a plurality of detectors arranged in rows and columns of detectors, a middle of a first detector separated from the middle of an adjacent second detector by a detector distance,
   the CT imaging system configured to:
      produce x-rays from a plurality of x-ray device positions and the plurality of focal spot positions,
      determine a first plurality of x-ray attenuation values based at least in part on the x-rays detected by the detector array,
      determine a second plurality of x-ray attenuation values, the second plurality of x-ray attenuation values associated with a plurality of levels, wherein the plurality of levels are spaced along the x-rays with respect to the radially shifted focal spot positions and at least one of the plurality of levels intersecting the examination region, the second plurality of attenuation values based at least in part on the first plurality of attenuation values, the plurality of x-ray device positions and the plurality of focal spot positions, and
      generate a volumetric image reconstruction of the examination region based at least in part on the second plurality of attenuation values associated with the plurality of levels.

16. The CT imaging system of claim 15, wherein the first focal spot position and the second focal spot position are further positioned such that x-rays detected from the first focal spot position and the second focal spot positions are longitudinally interleaved proximate a center of the examination region by one-and-a-half times the detector distance.

17. The CT imaging system of claim 15, wherein the steering device is further configured to selectively transversely shift the focal spot relative to the anode.

18. The CT imaging system of claim 15, wherein the first focal spot position and the second focal spot position are positioned such that the first area and the second area do not overlap.

19. The CT imaging system of claim 15, wherein the steering device is further configured to selectively radially shift the focal spot relative to the anode.

* * * * *